United States Patent [19]
Bhatta

[11] Patent Number: 5,152,768
[45] Date of Patent: Oct. 6, 1992

[54] ELECTROHYDRAULIC LITHOTRIPSY

[76] Inventor: Krishna M. Bhatta, 111 B Centre St., Brookline, Mass. 02146

[21] Appl. No.: 661,508

[22] Filed: Feb. 26, 1991

[51] Int. Cl.⁵ ............................................. A61B 17/22
[52] U.S. Cl. ..................................... 606/128; 606/32; 128/24 EL
[58] Field of Search ................... 606/127, 128, 32, 33; 128/24 A, 24 EL

[56] References Cited

U.S. PATENT DOCUMENTS

| | | | |
|---|---|---|---|
| 4,030,505 | 6/1977 | Tessler | 606/128 |
| 4,191,189 | 3/1980 | Barkan | 606/128 |
| 4,870,603 | 1/1990 | Filler | 128/24 EL |
| 4,927,427 | 5/1990 | Kriauciunas et al. | 606/128 |
| 4,960,108 | 10/1990 | Reicher et al. | 606/128 |
| 4,966,132 | 10/1990 | Nowacki et al. | 606/128 X |

FOREIGN PATENT DOCUMENTS 3328068 2/1985 Fed. Rep. of Germany ... 128/24 EL

Primary Examiner—Peter A. Aschenbrenner
Attorney, Agent, or Firm—Hayes, Soloway, Hennessey & Hage

[57] ABSTRACT

Method and apparatus for fracturing hard deposits such as urinary and biliary calculi and arteriosclerotic plaque in the human body. An elongate guide member having an apertured hollow adjacent its distal end is inserted within the body with the distal end positioned adjacent the target. A working fluid is supplied to the hollow, and an electric spark is discharged within the hollow from an external energy source for generating pulse waves in the working fluid. The resulting pulse waves express working fluid from the hollow to impinge on the target. Makeup fluid is supplied and the spark repeated. The method and apparatus also may be advantageously employed for dilating narrowing in hollow internal structure in the body.

5 Claims, 1 Drawing Sheet

ELECTROHYDRAULIC LITHOTRIPSY

FIELD OF THE INVENTION

The present invention relates to a system for fracturing hard formations in the body, and more specifically, to a method and apparatus for fracturing deposits such as urinary and biliary calculi as well as arteriosclerotic plaque in the body.

BACKGROUND OF THE INVENTION

Calciferous and similar deposits occur in body fluid passages of various types. Of particular interest are urinary and biliary calculi as well as arteriosclerotic plaque.

Electrohydraulic lithotripsy and laser lithotripsy systems frequently are used to fragment urinary and biliary stones. Both systems utilize plasma-induced stress waves to fragment calculi. Electrohydraulic lithotripsy produces a plasma through an electrical discharge (spark). Electrohydraulic lithotripsy systems are relatively inexpensive. However, with electrohydraulic lithotripsy systems, there is a potential for thermal damage to healthy tissues surrounding the target deposit. With laser lithotripsy, a plasma is produced when a portion of the laser energy is absorbed by the stone. However, laser lithotripsy systems are expensive. Also, in the case of laser lithotripsy, the sharp laser delivery fiber may cause damage if inadvertently jabbed into healthy tissue.

In my article with Rosen et al entitled "Effects of Shielded or Unshielded Laser and Electrohydraulic Lithotripsy on Rabbit Bladder" published in the Journal of Urology, Vol. 148, Pages 857–860, April 1990, I disclosed a plasma shield for use with either a pulsed laser lithotriptor or an electrohydraulic lithotriptor. As described therein, the hollow shield is provided using a hollow spring fitted with a metal end cap. The pulsed laser source or pulsed electrical voltage source located in the flexible guide provides a pulse of energy in the vicinity of the metal end cap to produce a rapid vapor expansion that causes the metal end cap to undergo a pulse-like movement as the vapor expands against the fluid medium of the passage to impart a high-velocity jack-hammer type impact on the target deposit.

While the plasma shield impact device as described in my aforesaid publication offers the advantages of protecting surrounding healthy tissue from direct laser-/EHL spark, and also eliminates inadvertent puncturing of healthy tissue by a sharply pointed laser delivery fiber, the metal end cap is prone to fragmentation, resulting in the formation of metal fines in the body cavity.

SUMMARY OF THE INVENTION

The present invention provides a method and apparatus for selectively fracturing hard deposits such as urinary and biliary calculi and atherosclerotic plaque which overcomes the aforesaid and other disadvantages of the prior art. In accordance with the present invention there is provided an electrohydraulic lithotripsy system in which a shock wave is generated directly in a fluid mass adjacent the target deposit, and the energy contained in the shock wave transferred, through the fluid, to the target deposit. More particularly, in accordance with the present invention, a flexible guide member is provided for insertion through a fluid-containing body passage or surgically created passage. The guide member is positioned with its distal end adjacent the target deposit. The flexible guide member has a hollow adjacent its distal end. In use, the hollow is filled with a working fluid, which is continuously replenished from an external source. Energy pulse waves are generated in the working fluid in the hollow adjacent the distal end of the guide member by means of an electrical discharge (spark), and the resultant shock wave expressed from the hollow through an opening in the distal end of the guide member and impinged directly on the deposit whereby to fracture or erode the deposit. In one embodiment of the invention, the flexible guide member distal end comprises a metallic body nozzle, and the electrical discharge (spark) is generated across the working fluid between a single electrode extending into the working fluid and the metallic body. In another embodiment of the invention, a pair of spaced electrodes extend into the hollow adjacent the distal end of the guide member, and the electrical discharge (spark) may be generated across the working fluid between the two spaced electrodes.

In a preferred embodiment of the invention, a nozzle is provided on the distal end of the guide member for focusing the resulting shock wave.

DESCRIPTION OF THE DRAWINGS

The invention will be more fully understood from the following solely exemplary detailed description taken in conjunction with the accompanying drawings, in which like numerals depict like parts, and wherein.

DETAILED DESCRIPTION OF THE INVENTION

The present invention contemplates a method and apparatus for fracturing or eroding hard deposits in fluid-containing body passages by means of hydraulic force.

Figure 1:
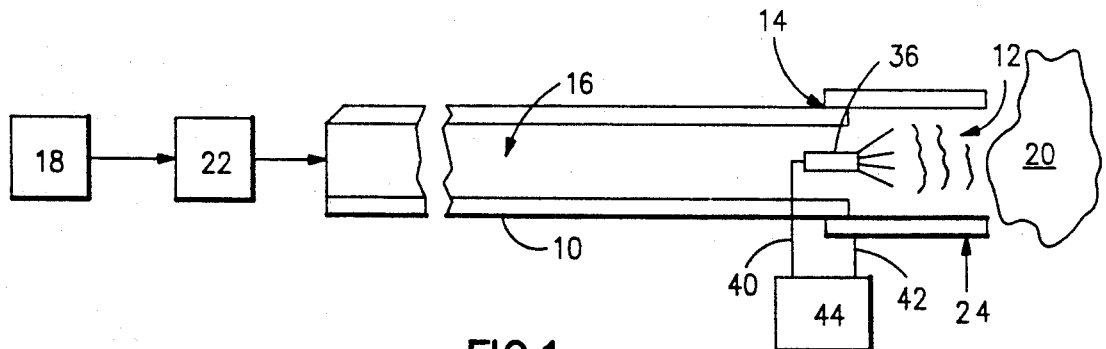
FIG. 1 is a block diagram of a preferred form of the invention.

Referring to FIG. 1, in accordance with the present invention, there is provided a guide member 10 having a hollow opening 12 at its distal end 14, and containing a working fluid 16 from a source 18. The guide member 10 comprises an elongate hollow tube, and is positioned with its distal end 14 adjacent, but spaced from, a target deposit 20 which may be a kidney stone arterial plaque or the like, and an electrical discharge spark is generated as will be described in detail hereinafter, in the working fluid adjacent the guide member distal end 14. Working fluid 16 comprises a biologically acceptable fluid such as 1/6 normal USP saline solution, which is flowed into guide member 10 by means of a pump 22.

Figure 2:
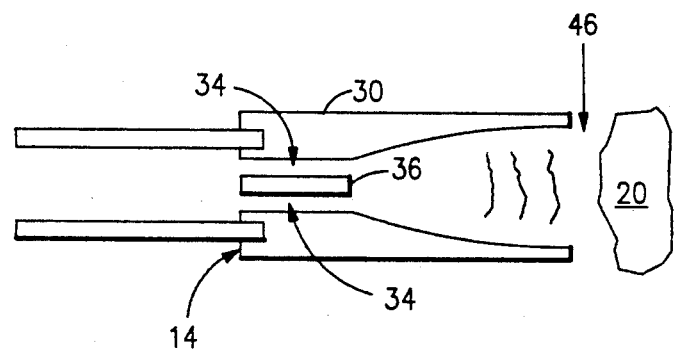
FIG. 2 is an enlarged view, in cross-section, and showing details of one embodiment of electrohydraulic lithotriptor device made in accordance with the present invention.

Guide member 10 may comprise a hollow tube as illustrated in FIG. 1, preferably comprising a metallic, hollow stub tube 24 mounted on the tube distal end 14. Alternatively, as shown in FIG. 2, an apertured metal nozzle 30, preferably of ellipsoid shape and typically formed of brass or stainless steel, may be mounted on the distal end 14 of tubing 10 in fluid communication with the working fluid source through one or more apertures 34 formed in the back wall of nozzle 30.

An electrode 36 is insulatively mounted, extending into nozzle 30 in communication with the working fluid contained therein. Electrode 36 is connected via conductor wire 40 to one terminal of a spark generator 44. A second conductor wire 42 connects the body of nozzle 30 to the other terminal of spark generator 44.

Spark generator 44, which may be any one of several commercially available spark generators such as a Wolfe 2137.50 or Northgate Research SDI, has its output applied on conductor wires 40 and 42. Spark generator 44 produces an output pulse of up to several microseconds, at several Kv and up to 1 Ka current. The spark generated between the tip of the electrode 36 and the metal nozzle body causes a vapor expansion of the working fluid contained within the nozzle adjacent the electrode tips which in turn causes a shock wave in the working fluid contained in the nozzle. Nozzle 30 shapes the resultant shock wave to a focal zone or focal point 46 permitting the resultant shock wave to fracture calciferous deposits upon which it impinges.

Figure 3:
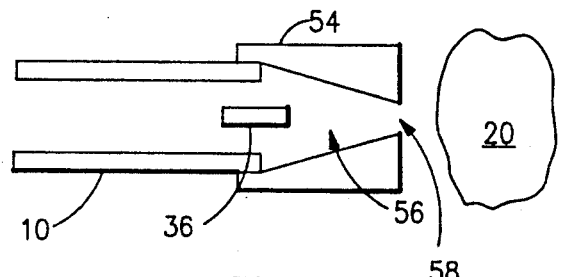
FIG. 3 is similar to FIG. 2, and illustrating details of another embodiment of electrohydraulic lithotriptor made in accordance with the present invention.
Figure 4:
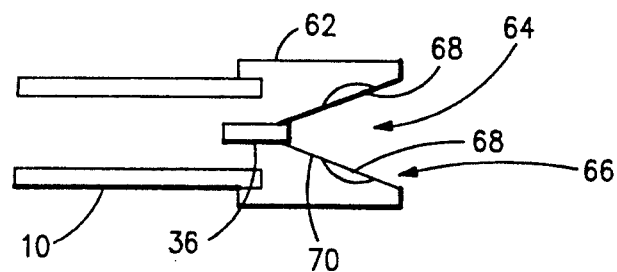
FIG. 4 is a view similar to FIG. 2, and illustrating details of yet another embodiment of electrohydraulic lithotriptor made in accordance with the present invention.

Referring to FIG. 3, there is shown yet another embodiment of the invention. In the FIG. 3 embodiment, the nozzle 54 may have an internal inverse conical hollow 56 narrowing to the end 58 of the nozzle. Alternatively, as shown in FIG. 4, the nozzle 62 may have an internal conical hollow 64 opening to the end 66 of the nozzle. One or more apertures 68 are formed in the back wall 70 of nozzle 62 for permitting replenishment of working fluid from the fluid source.

In use, the guide member or nozzle tip distal end is positioned in close spaced relation to the target deposit. Pump 22 is activated, whereby to force a continuous stream of working fluid into the nozzle hollow. The pulse generator is activated, providing a spark within the working fluid contained in the guide member or nozzle hollow. This spark, in turn, causes a rapid vapor expansion which, in turn, causes a pulse-like shock wave in the working fluid which is expressed from the hollow in pulsed shock waves to impinge directly on the target deposit to be removed. The pulsed shock waves impinging on the target nozzle fractures and erodes the target deposit.

A feature and advantage of the present invention is that only the working fluid and shock wave contacts the target deposit. Thus, the problems of impact tip fragmentation and metal fines formation experienced with metal tip impact lithotripsy devices of the prior art is eliminated. Also, since the spark is generated in a confined tube, the surrounding tissue is protected from the damaging effects of the plasma.

Various changes may be made in the above invention without departing from the spirit and scope thereof. For example, the tube distal end or nozzle may be formed of a hard, heat-resistant plastic such as Teflon. In such case the nozzle or tube distal end should be fitted with a pair of spaced electrodes, each connected via a conductor wire to one terminal of the spark generator 44, whereby a spark may be generated between the spaced electrodes. Also, the device may be dimensioned so as to provide a low energy spark which may be useful for resolving spasms in vessels, or to dilate narrowing of hollow internal structures.

It will therefore be understood that all matter herein described or shown in the accompanying drawings is to be interpreted as illustrative only, and is not to limit the invention defined in the following claims.

I claim:

1. Apparatus adapted for fracturing hard targets, reducing spasm in target vessels or dilating narrowing in hollow targets within a body characterized by comprising, in combination:

a flexible elongate guide member adapted for insertion within the body with the distal end thereof positioned adjacent a target, said guide member having an apertured hollow adjacent its distal end;

means for supplying a working fluid to said hollow from an external source;

a metallic, hollow tube mounted on the distal end of said guide member; and means for discharging an electric spark within said hollow tube from an external energy source for generating pulsed shock waves in the working fluid for impinging on said target.

2. Apparatus according to claim 1, wherein said hollow tube comprises a nozzle for shaping the fluid.

3. Apparatus according to claim 2, wherein said nozzle has an internal ellipsoid shape.

4. Apparatus according to claim 2, wherein said nozzle has an internal conical shape.

5. Apparatus according to claim 1, wherein said external energy source comprises a spark generator.

* * * * *